US009541485B1

(12) United States Patent
Rihan

(10) Patent No.: US 9,541,485 B1
(45) Date of Patent: Jan. 10, 2017

(54) SYSTEM FOR TESTING STRESS CORROSION CRACKING

(71) Applicant: KUWAIT INSTITUTE FOR SCIENTIFIC RESEARCH, Safat (KW)

(72) Inventor: Rihan Omar Yousef Rihan, Safat (KW)

(73) Assignee: KUWAIT INSTITUTE FOR SCIENTIFIC RESEARCH, Safat (KW)

( * ) Notice: Subject to any disclaimer, the term of this patent is extended or adjusted under 35 U.S.C. 154(b) by 0 days.

(21) Appl. No.: 15/237,600

(22) Filed: Aug. 15, 2016

(51) Int. Cl.
*G01N 3/08* (2006.01)
*G01N 17/00* (2006.01)

(52) U.S. Cl.
CPC .............. *G01N 3/08* (2013.01); *G01N 17/002* (2013.01); *G01N 17/006* (2013.01)

(58) Field of Classification Search
CPC ....... G01N 3/08; G01N 17/002; G01N 17/006
USPC .......................................... 73/799, 805, 826
See application file for complete search history.

(56) References Cited

U.S. PATENT DOCUMENTS

| 5,517,851 A * | 5/1996 | Berthold ................ G01N 17/00 73/86 |
| 5,883,311 A * | 3/1999 | Hettiarachchi ........ G01N 3/066 73/799 |
| 5,988,003 A | 11/1999 | Zuk |
| 8,173,959 B1 | 5/2012 | Sakaguchi et al. |
| 8,474,324 B2 | 7/2013 | Rihan et al. |
| 8,499,643 B2 | 8/2013 | Brown et al. |
| 2005/0167014 A1* | 8/2005 | Yamauchi ............ G01N 17/006 148/606 |
| 2010/0116382 A1* | 5/2010 | Kiuchi ................... C21D 6/004 148/608 |
| 2011/0248071 A1* | 10/2011 | Kiuchi ..................... B23K 9/04 228/119 |
| 2013/0133434 A1* | 5/2013 | Rihan .................. G01N 17/006 73/799 |

FOREIGN PATENT DOCUMENTS

FR 2 738 063 2/1997

OTHER PUBLICATIONS

Agboola et al., "Validation of Circumferential Notched Tensile (CNT) Test Procedure for KISCC Determination," *Proceedings of the World Congress on Engineering 2013* vol. III, WCE 2013, Jul. 3-5, 2013 London, U.K. (4 pages).

* cited by examiner

*Primary Examiner* — Max Noori
(74) *Attorney, Agent, or Firm* — Richard C. Litman

(57) ABSTRACT

The system for testing stress corrosion cracking (SCC) includes an autoclave having at least one heating element selectively actuated to heat the interior portion of the autoclave, the autoclave being configured for receiving a liquid and/or gas and for forming a corrosive fluid. The system also includes a circulation assembly having a flow line and a test section line. A plurality of test sections is positioned in series along the test section line and configured for receiving the corrosive fluid via the test section line once the required temperature is reached to expose the specimens directly to the corrosive fluid, the fluid flowing through a section of the flow line parallel to the test section line until the required temperature is reached. The circulation assembly includes a circulating pump, a flowmeter positioned along the flow line, and a pressure assembly mounted on the autoclave.

9 Claims, 2 Drawing Sheets

SYSTEM FOR TESTING STRESS CORROSION CRACKING

BACKGROUND OF THE INVENTION

1. Field of the Invention

The present invention relates to stress testing of materials, and particularly to a system for testing stress corrosion cracking (SCC) in metallic objects for monitoring purposes.

2. Description of the Related Art

Major industries, such as the oil and gas industry, the petrochemical industry, as well as desalination plants and power plants, experience stress corrosion cracking (SCC) problems. SCC refers to the growth of a crack formation in a corrosive environment and can result from a combination of factors, such as a susceptible material, a corrosive environment, and tensile stresses above a threshold level for that particular material. Various materials, such as metals, polymers, and ceramics, are susceptible to SCC, and the most common premature failures in these materials are typically the result of SCC. SCC of in-service components can occur in areas that are undetectable and/or difficult to access. Further, SCC is considered to be one of the most dangerous forms of failure due to the presence of stress and a corrosive environment, since the crack resulting from corrosion may propagate undetected and cause a leak or a sudden failure, resulting in catastrophic results. To counter such potential dangers, a complete shutdown may be necessary for maintenance and repair. Such actions can incur prohibitive costs, both from loss of production and maintenance that may be required.

Since cracking and failures in the vessels and in pipework in processing plants are ongoing problems, and since plant integrity is a major concern with regard to safety and the environment, engineers and designers must carefully assess various different materials to be used in making the components for an industrial environment. For example, engineers must determine the stress intensity factor ($K_I$) and the threshold stress intensity ($K_{ISCC}$) in the components made from those materials in order to determine the life expectancy of the components in corrosive environments, conformance to construction standards, and the ability of the component to meet performance demands.

Currently, there are various types of systems and methods used to investigate failed components and monitor SCC. For example, typically a testing unit involves the use of a specimen of material placed in a rig and exposed to tensile stress to measure the KI and the KISCC. However, the traditional fracture mechanic techniques require testing rigs that tend to be bulky and require a relatively large amount of space. The use of traditional testing rigs can be prohibitively expensive and time-consuming, both in terms of the device itself and the necessary upkeep and specialty needs. Further, conventional fracture specimens, such as compact tension (CT) specimens and pre-cracked double cantilever beam (DCB) specimens, are relatively expensive and bulky, requiring a rather large thickness to achieve plane strain conditions. Moreover, in some instances, these types of specimens cannot be obtained from failed components.

Therefore, the expense of both the machine and the specimens, as well as the large size of the traditional testing rigs can restrict their use for SCC monitoring. Further, many of the fracture mechanic techniques have been developed to examine SCC in the presence of stagnant (no flowing) water, which is not an actual condition in an industry where the fluid is usually in a flowing condition.

Thus, a system for testing stress corrosion cracking solving the aforementioned problems is desired.

SUMMARY OF THE INVENTION

The system for testing stress corrosion cracking (SCC) includes an autoclave having at least one heating element selectively actuated to heat the interior portion of the autoclave, e.g., up to 230° C., the autoclave being configured for receiving a liquid and/or gas and for forming a corrosive fluid. The system also includes a circulation assembly having a flow line (i.e., a by-pass line) and a test section line, the flow line being positioned in fluid communication with the autoclave and configured for circulating the corrosive fluid throughout the system during the heating process, and a plurality of test sections, each of the plurality of test sections being positioned in series along the test section line and configured for receiving the corrosive fluid via the test section line once the required temperature is reached to expose the specimens directly to the corrosive fluid at the required temperature. The circulation assembly also includes a circulating pump and a flowmeter positioned along the flow line, as well as a pressure assembly mounted on the autoclave, the pressure assembly being configured for admitting a pressurized gas into the autoclave.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
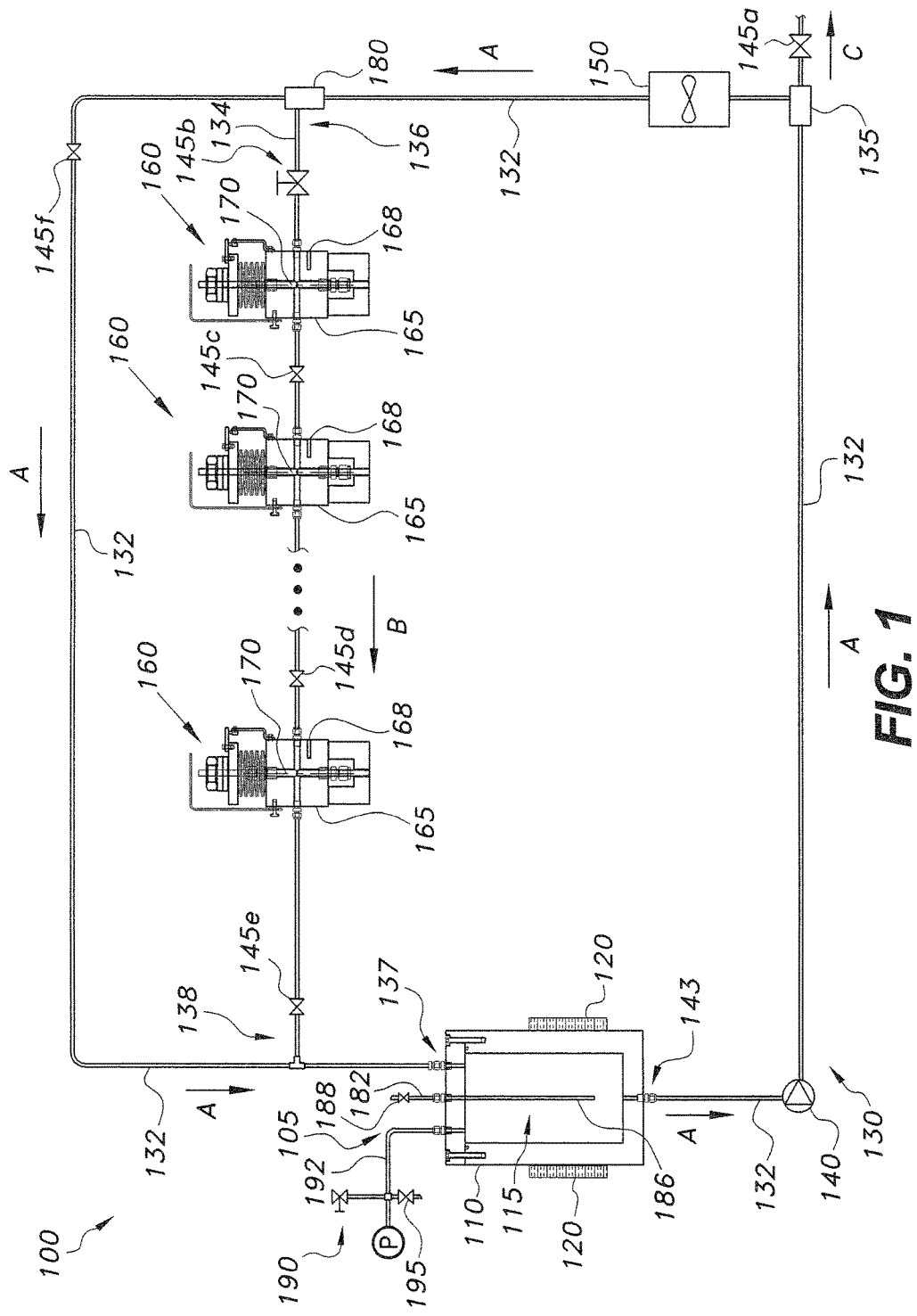
FIG. 1 is a schematic diagram of a system for testing for stress corrosion cracking according to the present invention, configured for circulating a heated corrosive fluid through the test cells.
Figure 2:
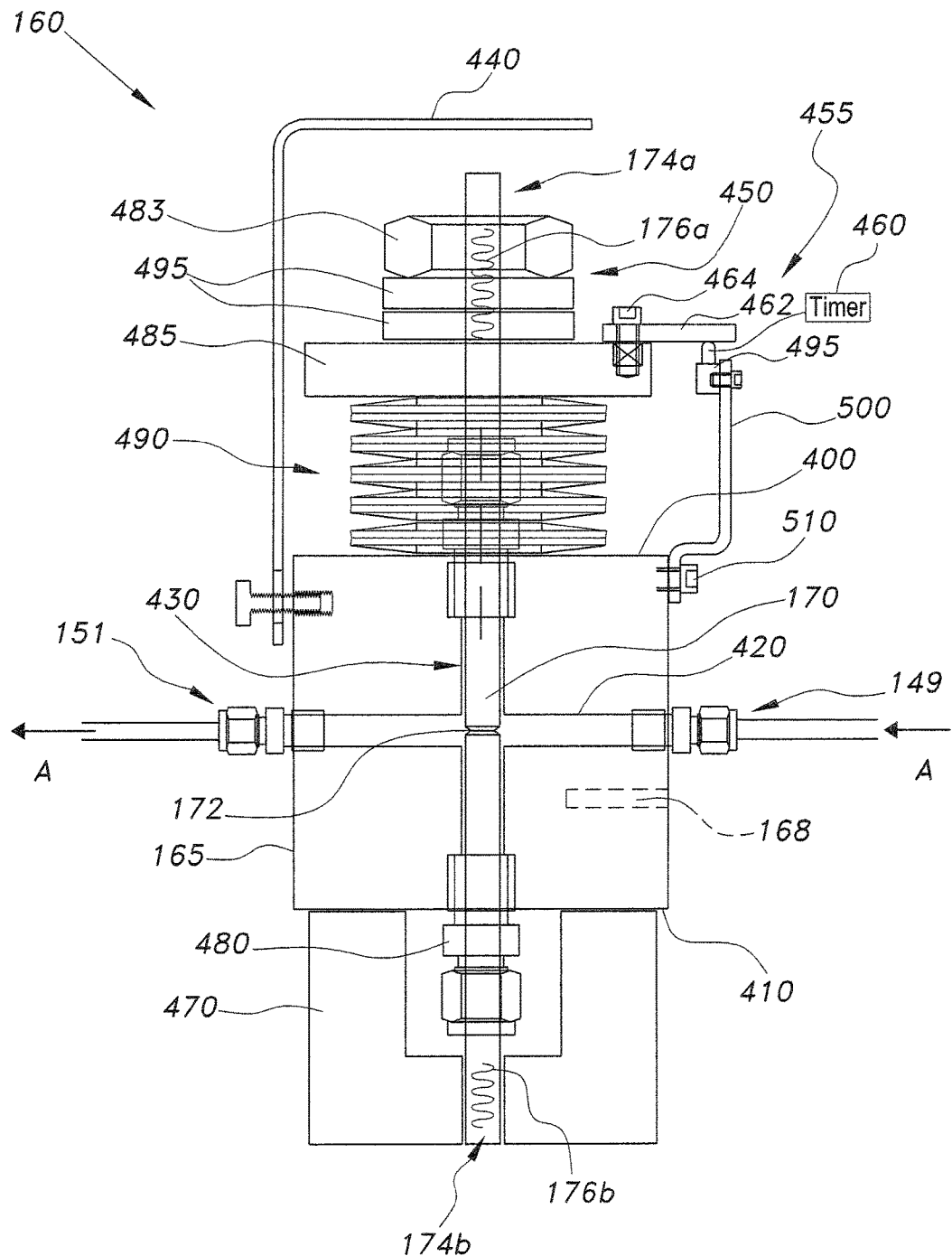
FIG. 2 is a diagrammatic side view of a test section for a system for testing for stress corrosion cracking according to the present invention.

Referring to FIGS. 1 and 2, a system 100 for testing stress corrosion cracking (SCC) is shown. The system 100 includes a pressure assembly 105 configured for admitting a pressurized gas and/or liquid into the system 100; an autoclave 110 having at least one heating element 120, the autoclave 110 being configured for receiving the pressurized gas and/or a liquid and for forming a corrosive fluid (e.g., liquid or gas); a circulation assembly 130 having a flow line 132 (i.e., a by-pass line) and a test section line 134, the flow line 132 being positioned in fluid communication with the autoclave 110 and configured for circulating the corrosive fluid throughout the system 100 during the heating process; and a plurality of test sections 160, each test section 160 being configured for holding a specimen 170 (preferably a circumferentially notched tensile (CNT) specimen) in a corrosive cell 165. The plurality of test sections 160 are positioned in series along the test section line 134 and configured for receiving the corrosive fluid via the test section line 134 once the required temperature is reached in order to expose each specimen 170 directly to the corrosive fluid at the required temperature. It is to be understood that the plurality of test sections 160 permits more specimens to be tested simultaneously.

The circulation assembly 130 also includes a first Tee fitting 135 and a second Tee fitting 180 positioned on the flow line 132, the Tee fittings 135, 180 being configured for joining the flow lines 132 and test section lines 134 together throughout the circulation assembly 130, as illustrated in FIG. 1. A circulation pump 140, such as a variable control speed pump, is configured to circulate the corrosive fluid throughout the system 100 and control the velocity of the corrosive fluid throughout the system 100. A flowmeter 150 is mounted along the flow line 132 of the circulation assembly 130, such as between the first Tee fitting 135 and the second Tee fitting 180, and is configured for measuring the velocity of the flow of the corrosive fluid throughout the system 100.

The circulation assembly 130 may also include a plurality of control valves, such as a first control valve 145a, such as a filling/draining valve, configured for filling the system with a fluid (e.g., distilled water or corrosive liquid) at the start of an experiment, and subsequently draining the system 100 of the corrosive fluid at the end of the experiment; a second control valve 145b; a third control valve 145c; a fourth control valve 145d; a fifth control valve 145e; and a sixth control valve 145f. The control valves 145b, 145c, 145d, and 145e are positioned along the test section line 134. For example, the second control valve 145b controls the flow of the corrosive fluid into the test section line 134 and into each of the plurality of test sections 160, whereas the fifth control valve 145e controls the flow of the corrosive fluid out of the test section line 134 and back into the autoclave 110 to recycle the corrosive fluid through the circulation system 130. The third control valve 145c and the fourth control valve 145d are positioned between consecutive test sections 160 to control the flow of corrosive fluid into each test section 160. The sixth control valve 145f is positioned along the flow line 132 and is configured for helping to control flow of the corrosive fluid throughout the circulation assembly 130.

The autoclave 110 can be formed from any suitable type of material, such as highly corrosion-resistant alloys, including stainless steel and high-nickel alloys, e.g., Hastelloy C276, Monel 400, and Inconel 600. The autoclave 110 can be any type of vessel having an interior portion 115 suitable to simulate the corrosive environment present in industry equipment and components, such as reactors, pressure vessels, and pipelines, by generating the corrosive fluid, e.g., an aqueous solution of sodium hydroxide. The autoclave 110 has an outlet port 143 configured for discharging the corrosive fluid into the circulation assembly 130 of the system 100, including through each of the plurality of test sections 160.

The at least one heating element 120 can be any type of suitable heating element, such as a controlled electric band heater, that can be selectively actuated to heat the corrosive fluid contained inside the autoclave 110 to a high temperature, such as up to 230° C., or other extreme temperatures typically experienced by industrial components that can give rise to potential component failure. The temperature(s) can be monitored and recorded by a thermocouple 168 disposed inside the corrosive cell 165 in each of the plurality of test sections 160.

The flow line 132 of the circulation assembly 130 can be detachably mounted onto the outlet port 143 of the autoclave 110 and to a return port 137 of the autoclave 110 by a sealed fitting. It is to be noted that the flow line 132 forms a circulation loop between the outlet port 143 of the autoclave 110 and the return port 137 of the autoclave 110.

The test section line 134 includes a first end 136 and a second end 138. The first end 136 of the test section line 134 is positioned in fluid communication with the second Tee fitting 180 positioned on the flow line 132, and the second end 138 of the test section line 134 is coupled to the flow line 132 such that the circulation pump 140 can re-circulate the corrosive fluid throughout the system 100 via the flow line 132 (the first control valve 145a, the second control valve 145b, and the fifth control valve 145e being closed and the sixth control valve 145f being open) until the corrosive fluid reaches the required temperature. Once the required temperature is reached, the sixth control valve 145f is closed, while the second control valve 145b, the third control valve 145c, the fourth control valve 145d, and the fifth control valve 145e are opened to divert the corrosive fluid into the test section line 134 and expose each of the specimens 170 directly to the corrosive fluid at the required temperature.

In the event that a specimen in a test section 160 fails, the pair of valves 145b-145e on opposite sides of the failed test section 160 may be closed, and the failed test section may be temporarily replaced with a connecting line or section of conduit. Opening the valves on opposite sides of the temporary connecting line permits the remaining test sections 160 to be operated for testing specimens until the failed test section is replaced. When the failed specimen is placed, the valves 145b-145e on opposite sides of the temporary connecting line are closed, the temporary connecting line is removed, and the failed test section (now with a new specimen) is reinserted in the test section line 134. The valves 145b-145e on opposite sides of the re-inserted test section 160 can then be opened for normal testing. Further, the flow line 132, as well as the test section line 134, can have any suitable diameter. For example, the nominal diameter of the flow line 132 and the test section line 134 of the circulation assembly 130 may be ⅜ inch.

The pressure assembly 105 can include a gas inlet 182 extending through a seal or other fastener or fitting in the autoclave 110. The gas inlet 182 may terminate in a bubbler tube 186 extending toward the bottom of the interior portion 115 of the autoclave 110 for efficient distribution of the pressurizing gas.

A gas inlet valve 188 can be operatively connection to the gas inlet 182 for selectively controlling the operation and rate of pressurizing gas flow into the autoclave 110. During operation, the pressure assembly 105 can pressurize the corrosion cell 165 in each respective test section 160 up to 85 bar, providing a pressure range in which actual industrial components operate.

The pressurizing gas can be allowed to escape through an outlet tube 192 extending from the autoclave 110. The gas outlet tube 192 can include a gas outlet valve 190 operatively attached thereto for selective control of gas outflow. A pressure gauge P or pressure transducer may be attached to the outlet tube 192 to measure, monitor, and record pressure inside the system. If the pressure exceeds a predetermined safe limit, a safety valve 195, such as a pressure relief valve, can permit automatic release of gas to relieve the pressure. The pressurizing gas may be carbon dioxide or nitrogen.

By way of operation, after the specimen 170 has been positioned in each of the plurality of test sections 160, the first control valve 145a (i.e., the filling/draining valve) and the sixth control valve 145f can be opened (the second control valve 145b being closed) to allow corrosive fluid to flow into the circulation assembly 130 to circulate through the autoclave 110 of the system 100. Once sufficient corrosive fluid has entered the system 100, the first valve 145a can be closed to prevent any corrosive fluid from draining from the system 100. The circulation pump 140 can then circulate the corrosive fluid from the autoclave 110 through the flow line 132 and return back to the autoclave 110 so that the corrosive fluid can mix with gas. The at least one heating element 120 can then heat the corrosive fluid to a desired temperature, such as up to 230° C. It must be noted that until the corrosive fluid reaches the desired temperature, the second control valve 145b and the fifth control valve 145e of the test section line 134 remain closed and the sixth control valve 145f of the flow line 132 remains open so that the corrosive fluid can circulate throughout the flow line 132 of the circulation assembly 130, as illustrated by arrows A, until the desired temperature is reached.

Once the desired temperature is reached, the sixth control valve 145f is closed and the second control valve 145b, along with the third control valve 145c, the fourth control valve 145d, and the fifth control valve 145e are opened to divert the flow of corrosive fluid into the test section line 134, such as via the first end 136 of the test section line 134, and into each of the plurality of test sections 160 to expose the specimens directly to the corrosive fluid, as illustrated by arrow B. Once the sixth control valve 145f is closed and the control valves 145b-145e are opened, the corrosive fluid can flow entirely through the test section line 134 and into the back into the autoclave 110. After each of the specimens 170 has been exposed to the corrosive fluid, the corrosive fluid can exit the test section line 134 via the second end 138 of the test section line 134, and can then be re-circulated throughout the system 100.

After the experiment has been completed, the first control valve 145a (i.e. the filling/draining valve) can be opened to drain the corrosive fluid from the system 100, as illustrated by arrow C.

Referring to FIG. 2, the corrosive cell 165 of each of the plurality of test sections 160 can be formed from any suitable type of material, such as highly corrosion-resistant alloys. The corrosive cell 165 can have an upper surface 400 and a bottom surface 410, and a flow channel 420 extending between an inlet port 149 and an outlet port 151, as illustrated by the arrow A. A central channel 430 configured for holding the specimen 170 for SCC testing therein extends orthogonal to the flow channel 420. It is to be noted that each of the plurality of test sections 160 can have different flow channel diameters to increase or decrease the flow velocity from one test section 160 to another.

The specimen 170 can have an upper portion 174a including an upper threaded end 176a, and a bottom portion 174b including a bottom threaded end 176b. Each of the plurality of test sections 160 can include a safety arm 440 configured for preventing the specimen 170 from being ejected as a projectile when the specimen 170 fails. A tensile loading assembly 450 holds the specimen 170 in the central channel 430 with the circumferential notch 172 in the path of corrosive fluid through the flow channel 420. A timing assembly 455 is positioned in communicating relation to the tensile loading assembly 450, the timing assembly 455 being configured for monitoring and measuring the time interval for the specimen 170 to break under load.

The bottom threaded end 176b of the bottom portion 174b of the specimen 170 may be secured by a specimen holding nut 470 positioned beneath the bottom surface 410 of the corrosive cell 165. The specimen holding nut 470 includes threads for holding the bottom threaded end 176b of the specimen 170. Each of the plurality of test sections 160 can include a sealed fitting 480 configured to seal the bottom surface 410 of the corrosion cell 165. The sealed fitting 480 can be disposed beneath the bottom surface 410 of the corrosive cell 165 for preventing leakage of the corrosive fluid at high temperatures and pressures. It is to be understood that another sealed fitting can be disposed above the top surface 400 of the corrosive cell 165 for preventing leakage of the corrosive fluid at high temperatures and pressures.

The upper portion 174a of the specimen 170 is secured to the tensile loading assembly 450, which can induce stress cracking on the specimen 170 by applying a constant tensile load on to the specimen 170 until the specimen 170 breaks in order to determine at least the stress intensity factor ($K_I$) and the threshold stress intensity factor ($K_{ISCC}$). The tensile loading assembly 450 can include an adjustment nut 483, a loading frame 485 loosely attached to the upper portion of the specimen 174a, and at least one Belleville spring 490 disposed between the loading frame 485 and the upper surface 400 of the corrosive cell 165.

The actual tensile force is provided by the at least one spring 490, preferably a plurality of Belleville spring washers. The at least one spring 490 can be used to exert a certain constant tensile load on the specimen 170. By way of operation, a downward force, such as by an external loading device or means, is forced against the loading frame 485 to compress or load the at least one spring 490 to a desired depth or amount of stored energy.

Once loaded, the adjustment nut 483, mounted above the loading frame 485, is threadably engaged onto the upper threaded end 174a of the specimen 170 and is adjusted and set to hold the loading frame 485 in position. The adjustment nut 483 can be adjusted upward or downward along the upper threaded end 174a of the specimen 170, as required by the user. Once the adjustment nut 483 is set, the external load or means can then be removed. The removal of the external load allows the stored energy in the at least one spring 490 to be transmitted to the specimen 170 as a tensile load by biasing the loading frame 485 upward, thereby stretching the specimen 170. To ensure that the tensile load is maintained axially, the tensile loading assembly may also include a plurality of self-alignment washers 497 disposed between the adjustment nut 483 and the load frame 485.

The timing assembly 455 may be configured for monitoring and measuring the time interval for the specimen 170 to break under load. The timing assembly 455 may include a micro switch 495 coupled to a mounting bracket 500. The mounting bracket 500 may be secured to the outside of the corrosion cell 165 by a first fastener 510. The micro switch can be electrically connection to a timer 460 configured for measuring the time interval between the closed circuit state and the open circuit state of the micro switch 495. As illustrated in FIG. 2, a contact arm 462 can be attached to the loading frame 485 by a second fastener 464.

During the test and before the specimen breaks, the electrical circuit is maintained in a closed state by having the contact arm 462 in contact with the micro switch 495. When the specimen 170 breaks, the loading frame 485 moves in an upward direction, which, in turn, correspondingly moves the contact arm 462 upward to thereby break contact with the micro switch 495 and open the circuit. Thus, the time to failure can be determined by measuring the interval between load release and specimen 170 failure.

It is to be understood that the present invention is not limited to the embodiments described above, but encompasses any and all embodiments within the scope of the following claims.

I claim:

1. A system for testing stress corrosion cracking (SCC), comprising:

an autoclave having at least one heating element, an outlet port, and a return port, the autoclave being adapted for heating a corrosive fluid;

a plurality of test sections, each of the test sections having:

a corrosive cell defining a test chamber;

an inlet port;

an outlet port;

a flow channel extending through the test chamber between the inlet port and the outlet port;

a central channel extending through the test chamber orthogonal to the flow channel, the central channel being configured for supporting a circumferentially notched tensile (CNT) specimen therein with the notch in the specimen exposed in the flow channel; and a tension loading assembly adapted for applying a constant tensile stress to the CNT specimen; and a circulation assembly having a circulation pump, a flow line forming a circulation loop between the outlet port of the autoclave and the return port of the autoclave and a test section line connecting each of the plurality of test sections connected in series, the flow line being in fluid communication with the test section line;

whereby the system is configured for testing a plurality of specimens for stress corrosion cracking in the presence of a flow of corrosive fluid being circulated by the circulation pump.

2. The system for testing stress corrosion cracking according to claim 1, further comprising a pressuring assembly mounted on the autoclave, the pressuring assembly being configured for admitting a pressurized gas into the system, whereby the system is configured for testing the specimens for stress corrosion cracking at high temperatures and high pressure.

3. The system for testing stress corrosion cracking according to claim 2, wherein said pressurizing assembly comprises:

a gas inlet valve configure for receiving a gas;

a gas outlet valve configured for releasing the gas; and a pressure transducer attached to the gas outlet valve.

4. The system for testing stress corrosion cracking according to claim 1, wherein the circulation assembly further comprises a flowmeter mounted along the flow line of the circulation assembly.

5. The system for testing stress corrosion cracking (SCC) according to claim 1, wherein each of the plurality of test sections comprises:

a specimen holding nut positioned beneath the corrosive cell, the specimen holding nut being configured for holding a lower threaded end of the specimen;

a safety arm configured for preventing the specimen from being ejected as a projectile when the specimen fails; and a timing assembly positioned in communicating relation to the tensile loading assembly, the timing assembly being configured for monitoring and measuring a time interval for the specimen to break under load.

6. The system for testing stress corrosion cracking according to claim 5, wherein the tensile loading assembly further comprises:

an adjustment nut adapted for threadable engagement with an upper threaded end of the specimen, the adjustment nut being selectively raised and lowered to adjust the tension load on the specimen;

a loading frame loosely attached to the upper portion of the specimen; and at least one spring disposed between the loading frame and the upper surface of the corrosive cell, the at least one spring being configured for biasing the loading frame upward to exert a tensile strength load on the specimen.

7. The system for testing stress corrosion cracking according to claim 6, wherein the at least one spring comprises a plurality of Belleville spring washers.

8. The system for testing stress corrosion cracking according to claim 7, wherein each of the plurality of test sections further comprises a plurality of self-alignment washers disposed between the adjustment nut and the load frame to maintain the tensile load axially.

9. The system for testing stress corrosion cracking according to claim 8, wherein the timing assembly further comprises:

a micro switch coupled to a mounting bracket;

a timer operatively connected to the micro switch; and a contact arm coupled to a fastener mounted to the loading frame, the contact arm being in selective contact with the micro switch, the contact arm normally being in contact with the micro switch to turn the timer on to measure failure time, contact between the contact arm and the micro switch being broken to stop the timer at the failure time when the specimen fails.

* * * * *